Figure 1:
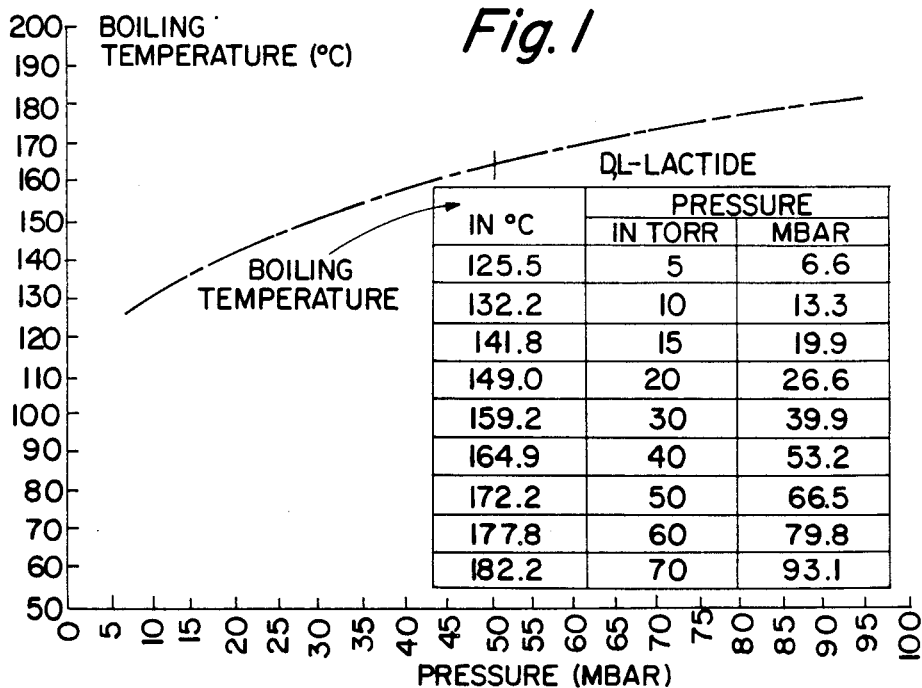
Figure 2:
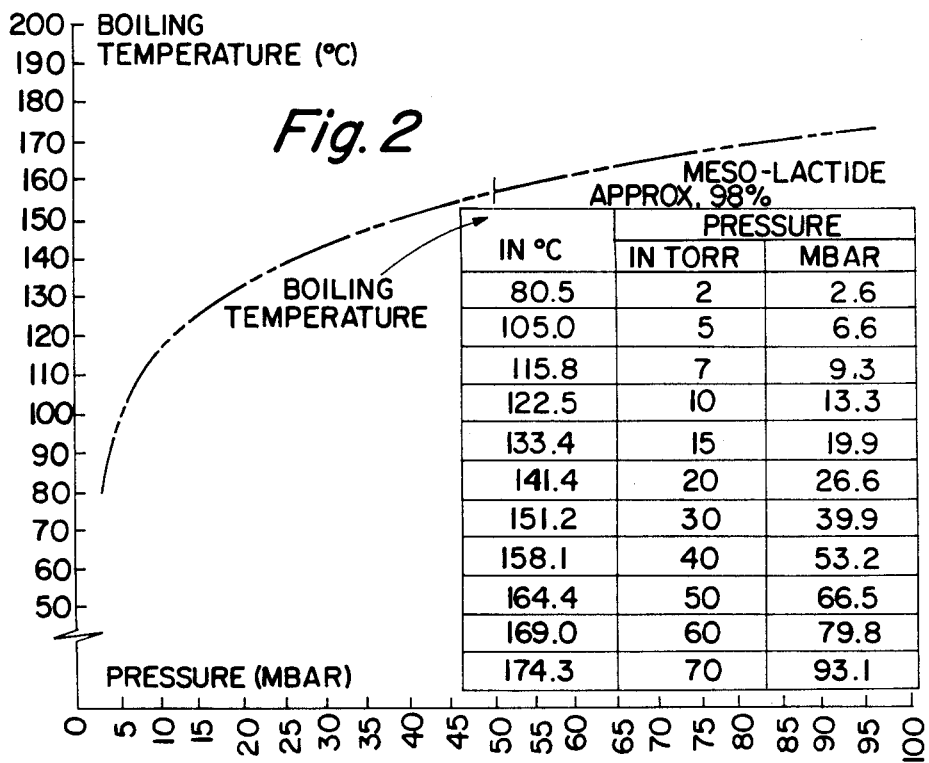
Figure 3:
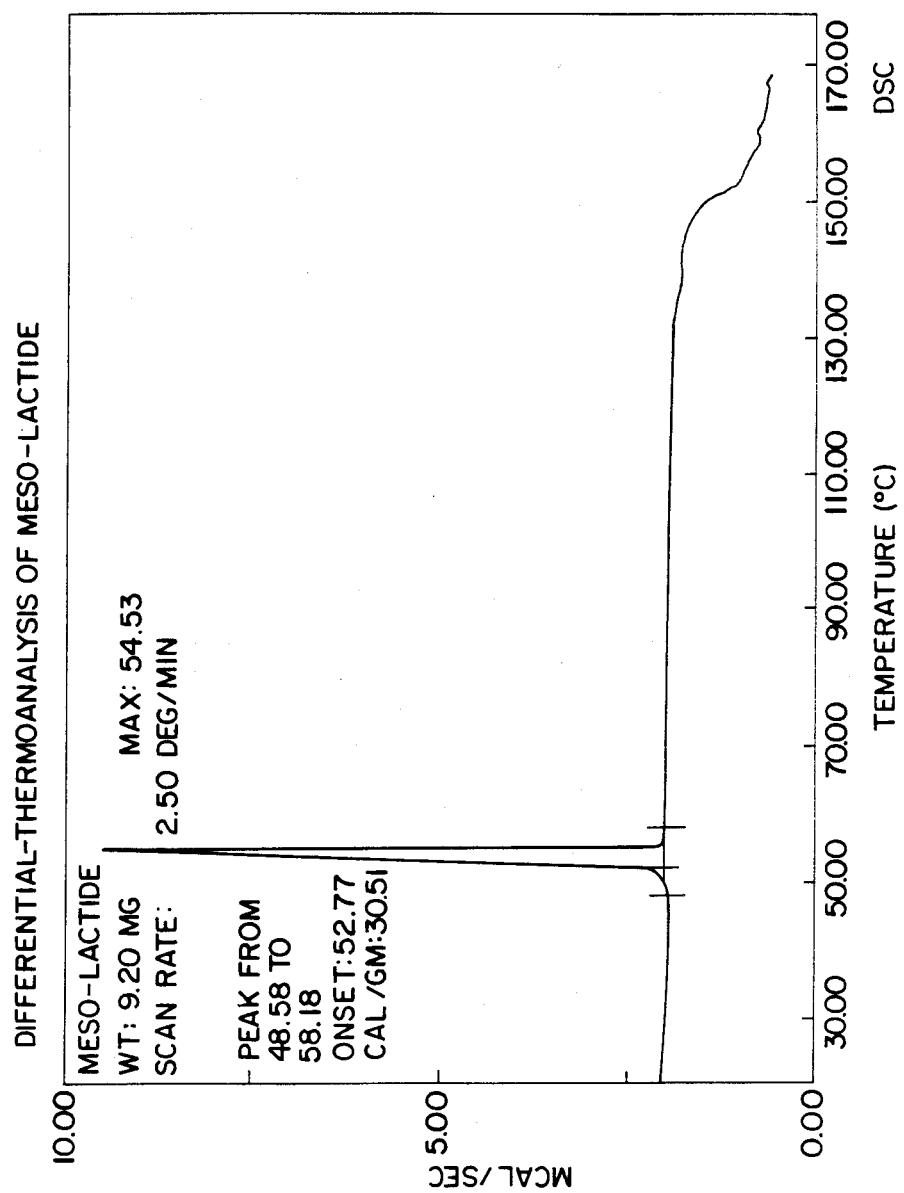
Figure 4:
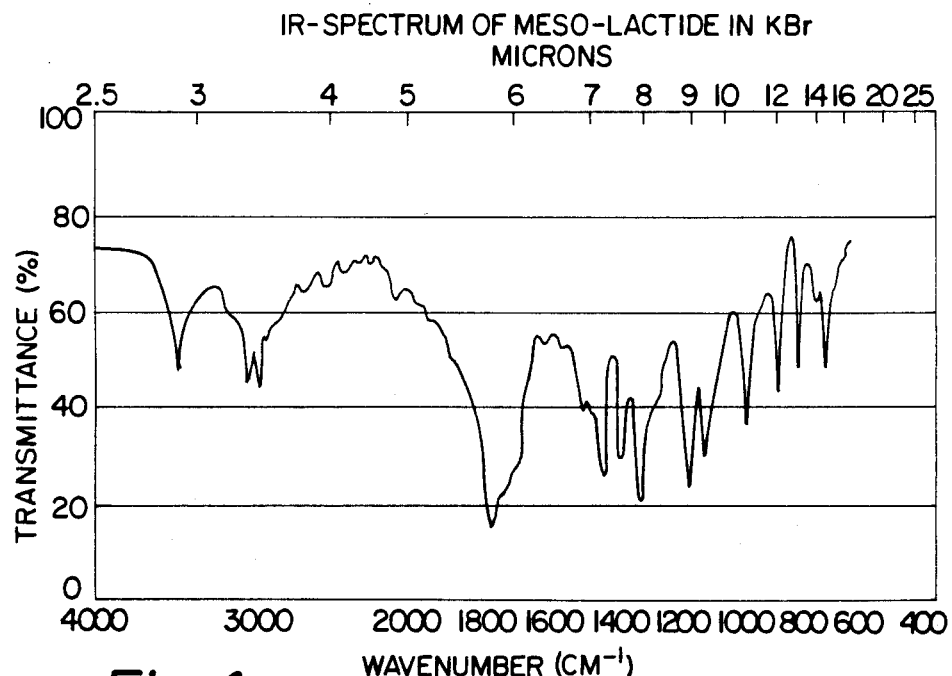
Figure 5:
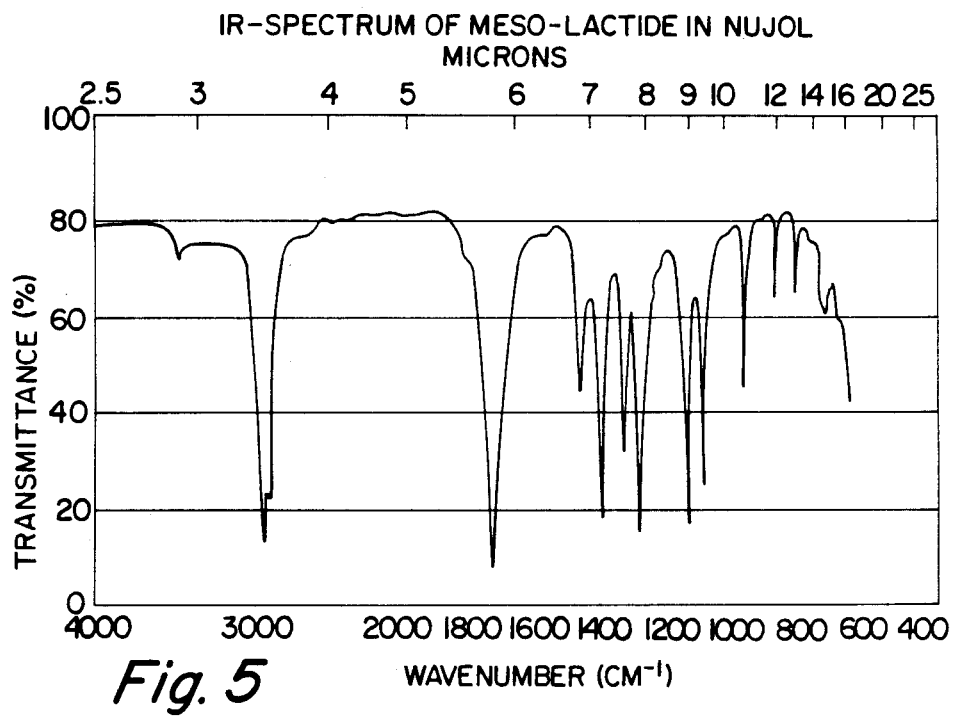

United States Patent [19]

Muller et al.

[11] Patent Number: 4,983,745

[45] Date of Patent: Jan. 8, 1991

[54] MESO-LACTIDE, PROCESSES FOR PREPARING IT AND POLYMERS AND COPOLYMERS PRODUCED THEREFROM

[75] Inventors: Manfred Muller, Bickenbach; Joachim Hess, Bingen; Wilhem-Gustav Schnell, Ingelheim am Rhein; Dieter Bendix, Ingelheim am Rhein; Gunther Entenmann, Ingelheim am Rhein, all of Fed. Rep. of Germany

[73] Assignee: Boehringer Ingelheim KG, Ingelheim am Rhein, Fed. Rep. of Germany

[21] Appl. No.: 335,089

[22] Filed: Apr. 3, 1989

[30] Foreign Application Priority Data

Jun. 16, 1987 [DE] Fed. Rep. of Germany ....... 3720060

[51] Int. Cl.$^5$ .......................................... C07D 319/12
[52] U.S. Cl. ...................... 549/274; 424/78; 424/426; 528/354; 606/60; 606/65; 606/86; 606/230; 606/231
[58] Field of Search ........................................ 549/274

[56] References Cited

FOREIGN PATENT DOCUMENTS 0261572 3/1988 European Pat. Off. .
0275581 7/1988 European Pat. Off. .
0261362 10/1988 Fed. Rep. of Germany .

OTHER PUBLICATIONS

Cowsar, Donald et al. "Poly(lactide–co–Glycolide) Microcapsules for Controlled Release of Steroids" CA 105:102505x (1986).

Khomyakov, A. K. et al. "Cationic Copolymerization of Glycolide with Optically Active and Racemic Lactide Under the Action of Tin Dichloride Dihydrate" CA 106: 102705h (1987).

*Primary Examiner*—Glennon H. Hollrah
*Assistant Examiner*—Amelia A. Owens
*Attorney, Agent, or Firm*—D. E. arankhouser; M.-a. M. Timbers; A. R. Stempel

[57] ABSTRACT

The invention relates to a meso-lactide having a melting point of 52.8° C., processes for its preparation, and its use in the preparation of resorbable polymers and copolymers.

1 Claim, 4 Drawing Sheets

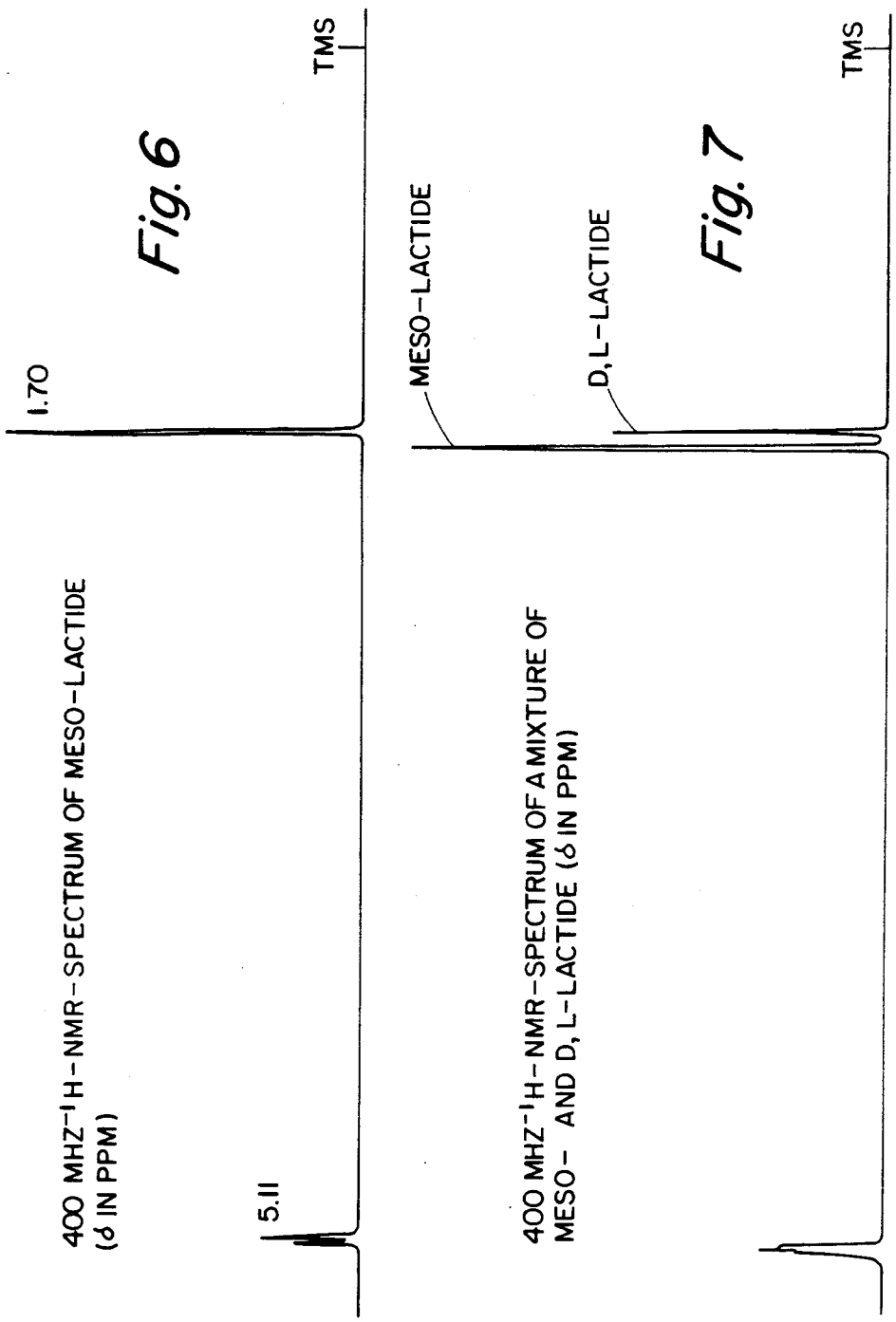

MESO-LACTIDE, PROCESSES FOR PREPARING IT AND POLYMERS AND COPOLYMERS PRODUCED THEREFROM

The invention relates to meso-lactide, processes for preparing it and its use in the production of polymers and copolymers.

Polymers based on lactic acid are of major importance in surgery and in wound dressing since these polymers are broken down in the body to form natural metabolic products. The possible applications of biodegradable polymers and copolymers are sufficiently well known from the prior art and need not be explained in detail here. Thus, for example, in the field of osteosynthesis, it is possible by using degradable polymers to avoid the second operations which have hitherto been necessary to remove any metal implants used. Now that it is known that the composition and manufacture (polymerisation conditions and speed of polymerisation) of the polymers has a considerable influence on the stability (tensile and bending strength) and degradation rate of the polymers, there is considerable interest in optically pure, well-defined monomers. In the case of the lactides, the corresponding dimeric cyclic esters are used as "monomers".

Whereas the "pure" compounds L(−), D(+) and racemic D,L-lactide are known, meso-lactide in pure form has hitherto been unknown. In the literature, the definition of D,L-lactide and meso-lactide has not always been adhered to strictly in terms of correct nomenclature. For the purposes of this invention, the term meso-lactide is used to denote the cyclic diester of lactic acid I,

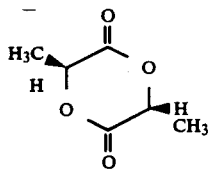

which has two centres of asymmetry with opposite configurations R and S.

The aim of this invention is to provide a "pure" meso-lactide which can be used as a monomer to produce biodegradable polymers and copolymers.

This is achieved according to the invention by rectifying a mixture of D,L-lactide and meso-lactide under reduced pressure. A pure meso-lactide with a melting point of 52.8° C. is obtained from the first distillate after recrystallisation.

Hitherto, only a meso-lactide with a melting point of 41° to 45° C. has been known from the literature.

The starting material is prepared as follows: racemic polylactic acid (50:50/D:L) is heated to 130° to 230° C. under reduced pressure in the presence of a suitable catalyst, e.g. in the presence of 0.05 to 1.0% by weight of powdered tin, $Sn^{2+}$ salts or an organic tin compound derived from a carboxylic acid with up to 20 carbon atoms, the lactide formed is distilled off and polylactic acid is added continuously or in batches.

Tin compounds which are particularly suitable for use as catalysts are compounds having the general structure

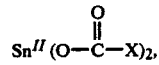

wherein X represents a branched or unbranched alkyl or alkenyl group with up to 19 carbon atoms or a naphthyl group, or compounds of general structure

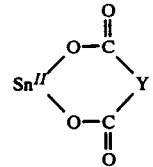

wherein Y represents a branched or unbranched alkylene or alkenylene group with up to 18 carbon atoms or a phenyl group.

Preferred catalysts are tin tartrate, tin oxalate, tin dicaprylate, tin dilaurate, tin dipalmitate, tin distearate, tin dioleate (derivative of oleic acid), tin-α-naphthoate or tin-β-naphthoate. Tin dioctoate, or more precisely tin di-(2-ethyl-hexanoate), or powdered tin are particularly preferred.

The racemic polylactic acid used in the process can be produced in a separate reaction step by known methods by dehydrating racemic lactic acid.

In another embodiment of the process, lactic acid is used instead of the polylactic acid. In a first reaction step, the lactic acid is dehydrated in the presence of the catalyst under reduced pressure at increasing temperature. In general, dehydration is carried out under pressures of about 10 to 50 hPa, with the temperature in the reactor rising to about 150° to 170° C. When the average molecular weight of the polylactic acid formed has reached about 400 to 2000, preferably 600–800, lactide is continuously distilled off and then polylactic acid is added continuously or in batches.

In another embodiment, lactic acid may be added to the continuous process instead of polylactic acid.

When the reactor is started up, racemic polylactic acid is put in and 0.05 to 1.0% by weight, preferably 0.1 to 0.8% by weight of tin dust or the organo-tin compound is added. Then the mixture is heated to 130° to 230° C., preferably 180° to 200° C., under reduced pressure, and the crude lactide produced, i.e. a mixture of D,L-lactide and meso-lactide, is distilled off. The optimum temperature range depends on the vacuum applied and can be determined by simple experiments. The lowest possible distillation temperature has a favourable effect on the purity of the distillate. After a certain amount of product has been distilled off, the reaction mixture is topped up with racemic polylactic acid. This is preferably added in molten form. It may be added in batches or continuously, e.g. by pumping. The total amount after topping up may be greater than the original quantity used at the start of the reaction.

If the racemic polylactic acid is being added in batches, the residual volume of the reactor content is non-critical over a wide range with regard to the quality of the product, although it is advisable to top up after about a 50 to 90% conversion. If the content of the reactor falls too far, it is possible that the product will deteriorate. If the product is fed in continuously, this will preferably be carried out so that the volume of the reactor content is kept as constant as possible.

If instead of racemic polylactic acid, racemic lactic acid is introduced directly into the reactor, before the depolymerisation producing the crude lactide occurs, the lactic acid is dehydrated in the presence of the catalyst of the organo-tin compound or the tin dust to form polylactic acid up to an average molecular weight of about 400 to 2000, preferably 500 to 800. Dehydration is preferably carried out at about 30 hPa whilst the temperature rises to about 170° C. After the desired molecular weight has been reached, the mixture is further processed as described hereinbefore.

As already mentioned, in another alternative embodiment racemic lactic acid may be added instead of racemic polylactic acid, in which case water will first be distilled out of the reaction mixture until the polylactic acid has the desired molecular weight. The process then continues as described above.

The initial use of lactic acid or topping up with lactic acid instead of polylactic acid has no disadvantages in terms of yield compared with the embodiments described hereinbefore. One advantage is the fact that the reaction time for dehydrating the lactic acid is shortened by about 50%. The molecular weight of the polylactic acid produced is determined by titration of the end groups.

The crude lactide distilled off, which consists of a mixture of meso and D,L-lactide, is then first precipitated from a $C_1$ to $C_4$ alcohol (such as methanol, ethanol, n-propanol, isopropanol), preferably isopropanol. The crystals thus obtained, consisting of a mixture of meso and D,L-lactide, are then recrystallised first from a $C_1$ to $C_4$ alcohol (e.g. methanol, ethanol, n-propanol, isopropanol), preferably isopropanol. The second crystals thus obtained are then dissolved in a halogenated hydrocarbon, preferably chloroform, particularly preferably 1,2-dichloroethane, or an aliphatic ether, preferably diethylether, from which D,L-lactide is then crystallised out. The mother liquor remaining, consisting of a mixture of meso-lactide and D,L-lactide in a ratio of about 60:40, is concentrated by evaporation and the residue is rectified according to the invention for further separation. The meso-lactide according to the invention is obtained from the first distillate. If desired, this may be recrystallised to purify it further. Preferred solvents are $C_{1-4}$ alcohols, preferably isopropanol, or toluene. This recrystallisation serves primarily to eliminate the free acid which is formed in small amounts during distillation.

It goes without saying that the first run is discarded before the desired first distillate of meso-lactide is obtained. The first run generally consists of solvent residues originating from the evaporation of the mother liquor and possibly small amounts of reaction products of the solvent with the lactide, such as, for example, isopropylester, if isopropanol has been used as the solvent. Rectification may be carried out with distillation columns in accordance with the prior art, having a specific minimum separation performance (number of plates, variable reflux ratio). A theoretical minimum number of plates required to separate two or more components is generally obtained from the difference in boiling point between the components which are to be separated.

As can be seen from the diagrams of the boiling point curves (FIGS. I and II), the boiling points of pure meso-lactide and D,L-lactide differ by about 7° C. over a wide range of pressures. This means that it is possible to carry out distillative separation of the two lactides with distillation columns having a theoretical minimum number of plates of about 30 to 40. The correlation between the theoretical number of plates and the actual separation performance, the practical number of plates, of a column depends on a number of factors but can be determined by simple experiments. If this minimum number of plates cannot be achieved with the apparatus used, distillation will have to be carried out several times.

The meso-lactide prepared by the process according to the invention is characterised by the following physical parameters.

Melting point 52.77° C. determined by the DTA method (differential thermo-analysis) (FIG. IIa) GC: 99.8% meso-lactide, 0.2% D,L-lactide (separation by gas chromatography)

$[\alpha]_D^{20} = 0°$

IR (measured in KBr and as a film in Nujol) FIGS. IIIa and IIIb $^1$H-NMR (400 MHz) see FIGS. IVa and IVb A meso-lactide of this purity has not been known hitherto and is claimed as such.

The meso-lactide according to the invention is particularly suitable for the preparation of defined polymers and copolymers on account of its optical purity.

Within the scope of the invention is included more particularly a poly(meso-lactide) prepared from the "pure" monomer according to the invention, and also a copolymer prepared by polymerisation of meso-lactide using the monomer listed below.

Suitable compounds for this purpose are 1,3-dioxan-2-ones of structure II, 1,4-dioxan-2-ones of structure III, lactides of structure IV and lactones of structure V

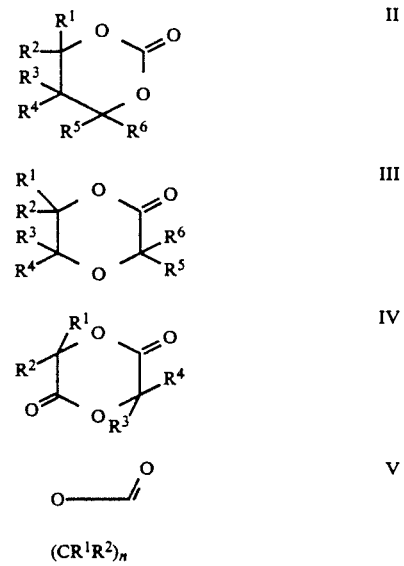

In structural formulae II to V, $R^1$, $R^2$, $R^3$, $R^4$, $R^5$ and $R^6$ may be identical or different and may represent hydrogen, a branched or unbranched alkyl, alkenyl or alkynyl group with 1 to 12, preferably 1 to 4 carbon atoms, which may optionally be substituted by halogen, preferably chlorine, bromine or iodine, or by hydroxy, a branched or unbranched alkoxy group with 1 to 4 carbon atoms or a formyl group; by an acyl group with 1 to 5 carbon atoms, a carboxyl group, an amino group, an alkylamino, dialkylamino or quaternary amino group preferably with 1 to 4 carbon atoms; they may also represent a cycloalkyl group with 3 to 6 carbon atoms which may be substituted like an alkyl group, a formyl group, an acyl group with 1 to 5 carbon atoms, a branched or unbranched alkoxycarbonyl group with 1 to 5 carbon atoms in the alkoxy group, an optionally substituted aryl or hetaryl group with 6 to 12 carbon atoms in the ring system and n represents one of the numbers 2, 3, 4, 5, 6, 7, 8, 9 or 10. By halogen is meant an atom selected from the group comprising fluorine, chlorine, bromine or iodine, and unless otherwise stated the preferred alkyl groups are methyl, ethyl, propyl, isopropyl, butyl, tert.butyl, whilst preferred aryl groups are phenyl or substituted phenyl. It goes without saying that groups having equal carbon atoms should be selected so as to enable the preparation of compounds of general formulae II to V by the methods of the prior art.

Preferred monomers are: L-lactide, D-lactide, D,L-lactide, glycolide, trimethylenecarbonate and 1,4-dioxanone.

The ratio of the monomers may be selected within a wide range from 1-99 to 99-1 mol % (mesolactide: monomer).

Preferred copolymers are:
poly(meso-lactide-co-L-lactide),
poly(meso-lactide-co-D-lactide),
poly(meso-lactide-co-D,L-lactide)
poly(meso-lactide-co-glycolide)
poly(meso-lactide-co-trimethylenecarbonate).

The invention claims not only random polymers but also block polymers.

Unlike known polymesolactides obtained from monomers which have a melting point of about 45° C, the polymesolactide according to the invention has a purely syndiotactic structure.

The polymers prepared according to the invention may be used, for example, for preparing stitching materials, active substance carriers, surgical implants—plates, screws and pins for fixing bone elements—protheses and filling materials—nets and films for reconstructing soft areas—films, foamed films and powders for wound treatment.

The polymers and copolymers claimed according to the invention may be prepared from the monomers described above analogously to known methods. These include methods carried out in a melt, in solution or in suspension.

Suitable polymerisation catalysts include, for example, organic tin compounds, preferably tin octoate (tin-di(2-ethylhexanoate) and tin salts such as tin(II) chloride. The duration of the reaction of polymerisation is generally between 1 and 72 hours; the reaction temperature is between 100° and 180° C.

The invention will hereinafter be illustrated by means of some Examples.

EXAMPLES OF THE PREPARATION OF MESO-LACTIDE

EXAMPLE 1

920 kg of racemic lactic acid with a content of about 90% are dehydrated at a sump temperature of about 180° C. and at about 10 hPa. 700 kg of racemic polylactic acid are obtained with an average molecular weight of 600.

EXAMPLE 2

430 kg of racemic polylactic acid with an average molecular weight of 600 are mixed with 3.5 kg of the tin(II) salt of 2-ethylhexanoic acid (tin dioctoate) and heated to 194°-198° C. under a vacuum of 33-17 hPa. D,L-lactide and meso-lactide are distilled off. After a quantity of 374 kg of lactide has been distilled, 270 kg of the polylactic acid described above are added and 252 kg of lactide are obtained under the conditions described.

Residue: 20 kg
Throughput: lactide: about 40 kg/h

The distillate of 626 kg is precipitated in an equal quantity of isopropanol and centrifuged. 545.6 kg of lactide are obtained (in moist form). This is recrystallised from 818 kg of isopropanol, centrifuged and dried. 395 kg of a mixture of D,L- and meso-lactide are obtained. This mixture is recrystallised from 198 kg of 1,2-dichloroethane, centrifuged and dried. 241 kg of D,L-lactide are obtained in the form of crystals, which are recrystallised from 362 kg of toluene to yield 219 kg of D,L-lactide (33.1%, based on the lactic acid put in).

Appearance: white crystals
Rotation: 0.0°
Melting point: DTA 124.6° C.
Water: 0.012%
Content: after saponification: 99.6%
Free acid: 0.001%
GC 0.15% toluene The crystals contain exclusively D,L-lactide and are virtually free from meso-lactide.

EXAMPLE 3

The mother liquor obtained in the recrystallisation of D,L-lactide from 1,2-dichloroethane (Example 2) is evaporated down to the residue and 147 kg of isopropanol are added. After about 31 kg of isopropanol have been distilled off, the remainder is cooled and the crystal slurry obtained is centrifuged and dried. 120.4 kg (18.2% based on the lactic acid used) of meso-lactide are obtained, with a content of about 63%. (Remainder =D,L-lactide)

EXAMPLE 4

8000 g of meso-lactide (according to Example 3) with a content of about 63% are rectified in a distillation column of l=1.80 m, 0=40 mm, filled with gauze rings 6/6 mm, at 8 hPa and a sump temperature of 147° C. and a reflux ratio of 15:1. 3985 g (75.1% of theory) of 95% meso-lactide are obtained.

EXAMPLE 5

8050 g of meso-lactide (according to Example 3) with a content of about 63% are rectified in a distillation column of l=1.80 m, 0=40 mm filled with gauze rings 6/6 mm, at 4 hPa and a sump temperature of 147° C. and a reflux ratio of 10:1. 3650 g (64.8% of theory) of 89.1% meso-lactide are obtained.

EXAMPLE 6

9271 g of 89.1% meso-lactide are rectified again under the conditions specified above. 3923 g of meso-lactide are obtained, which are recrystallised from 4000 g of isopropanol. After drying, 3786 g of 99.6% meso-lactide are recrystallised from 3860 g of toluene. After drying, 2969 g (35.9% of theory) of meso-lactide of the following quality are obtained:

Appearance: white crystals
Rotation: 0°

Melting point: DTA 52.77° C. (measured with DSC 2 made by Perkin Elmer in covered aluminium pans with a hole).
Water: 0.0265%
Free acid: 0.055%
GC 99.8% meso-lactide 0.2% D,L-lactide Examples of the preparation of polymers and copolymers from meso-lactide Comparison Example Two 20 g samples of a meso-lactide with a melting point of 42° C., a rotation value $\alpha_D^{20}$ of 0°, a water content of 0.06% and a free acid of 0.62% are polymerised in vacuo at 105° C. for 72 hours with the addition of 137.5 ppm of tin in the form of tin(II)octoate as catalyst.

The polymers obtained are characterised by determining the inherent viscosity (I.V.) in chloroform at 25° C. in a concentration of 0.1 g/dl:
Sample 1: I.V.=0.83 dl/g
Sample 2: I.V.=0.88 dl/g

EXAMPLE 7

Two 20 g samples of a meso-lactide with a melting point of 52.8° C. (onset in TLC), a rotation $\alpha_D^{20}$ of 0°, a water content of 0.03% and a free acid of 0.06% are polymerised in vacuo for 72 hours at 105° C. with the addition of 550.0 ppm of tin in the form of tin(II)octoate as catalyst.

The polymers obtained are characterised by determining the inherent viscosity (I.V.) in chloroform at 25° C. in a concentration of 0.1 g/dl:
Sample 1: I.V.=2.59 dl/g
Sample 2: I.V.=2.41 dl/g The residual monomer content, determined by a 400 MHz $^1$H-NMR, -measured in deuterochloroform, is 1.9% by weight.

EXAMPLE 8

Two 5 g samples of a meso-lactide with a melting point of 52.8° C. (onset in TLC), a rotation $\alpha_D^{20}$ of 0°, a water content of 0.03% and a free acid of 0.06% are polymerised in vacuo for 8 hours at 160° C. with the addition of 117.2 ppm of tin in the form of tin(II)octoate as catalyst.

The polymers obtained are characterised by determining the inherent viscosity in chloroform and dioxan at 25° C. and in hexafluorisopropanol (HF IP) at 30° C., in a concentration of 0.1 g/dl in each case:

|  | I.V. (CHCl$_3$) [dl/g] | (Dioxan) [dl/g] | (HFIP) [dl/g] |
|---|---|---|---|
| Sample 1 | 0.68 | 0.59 | 1.08 |
| Sample 2 | 0.70 | 0.57 | 1.03 |

EXAMPLE 9

A 1 kg sample of a meso-lactide with a melting point of 52.8° C. (onset in TLC) a rotation $\alpha_D^{20}$ of 0°, a water content of 0.03% and a free acid of 0.06% is polymerised at 105° C. in vacuo for 72 hours with the addition of 137.5 ppm of tin in the form of tin(II)octoate as catalyst.

The block of polymer obtained is characterised by determining the inherent viscosity in chloroform at 25° C. in a concentration of 0.1 g/dl:
I.V.=2.61 dl/g The residual monomer content, determined by a 400 MHz $^1$H-NMR, measured in deuterochloroform, is 1.7% by weight.

The spectrum furthermore shows a syndiotactic structure of the polymer.

The material has a bending strength of more than 140 N/mm$^2$.

EXAMPLE 10

2.77 g (50 mol %) of a meso-lactide with a melting point of 52.8° C. (onset in TLC), a rotation $\alpha_D^{20}$ of 0°, a water content of 0.03% and a free acid of 0.06% and 2.23 g of glycolide (50 mol %) is polymerised at 160° C. in vacuo for between 1 and 6 hours with the addition of 117.2 ppm of tin in the form of tin(II)octoate as catalyst.

The copolymers obtained are characterised by determining their inherent viscosity in chloroform and dioxan at 25° C. and in hexafluorisopropanol (HFIP) at 30° C., in a concentration of 0.1 g/dl in each case:

| Time [h] | I.V. (CHCl$_3$) [dl/g] | (Dioxan) [dl/g] | (HFIP) [dl/g] |
|---|---|---|---|
| 1 | 0.88 | 0.91 | 1.83 |
| 2 | 0.87 | 0.90 | 1.76 |
| 3 | 0.87 | 0.88 | 1.69 |
| 5 | 0.81 | 0.81 | 1.58 |
| 6 | 0.82 | 0.86 | 1.60 |

EXAMPLE 11

2.26 g (40 mol %) of a meso-lactide with a melting point of 52.8° C. (onset in TLC), a rotation $\alpha_D^{20}$ of 0°, a water content of 0.03% and a free acid of 0.06% and 2.23 g of glycolide (60 mol %) are polymerised at 160° C. in vacuo for between 1 and 6 hours with the addition of 117.2 ppm of tin in the form of tin(II)octoate as catalyst.

The copolymers obtained are characterised by determining their inherent viscosity in chloroform and dioxan at 25° C. and in hexafluorisopropanol (HFIP) at 30° C. in a concentration of 0.1 d/gl in each case:

| Time [h] | I.V. (CHCl$_3$) [dl/g] | (Dioxan) [dl/g] | (HFIP) [dl/g] |
|---|---|---|---|
| 1 | n.n. | 0.98 | 2.01 |
| 2 | n.n. | 1.02 | 2.04 |
| 3 | n.n. | 0.98 | 2.04 |
| 5 | 0.82 | 1.06 | 2.04 |
| 6 | 0.81 | 0.98 | 1.97 | n.n. = insoluble in chloroform.

What is claimed:

1. Process for preparing meso-lactide, characterised in that racemic polylactic acid is depolymerised in the presence of tin, tin salts or organic tin compounds as catalyst, the lactide formed is recrystallised in order to separate off a quantity of D,L-lactide, the mother liquor remaining is concentrated by evaporation and the residue is rectified, the first distillate obtained being the meso-lactide, which optionally is recrystallised.

* * * * *